(12) United States Patent
Labriola

(10) Patent No.: US 6,407,240 B1
(45) Date of Patent: Jun. 18, 2002

(54) PROCESS FOR PREPARING N,N,6-TRIMETHYL-2-(4-METHYLPHENYL)-IMIDAZO- [1,2-A]-PYRIDINE- 3-ACETAMIDE AND SALTS THEREOF

(75) Inventor: Rafael Labriola, Buenos Aires (AR)

(73) Assignee: Quimica Sintetica, S.A., Barcelona (ES)

( * ) Notice: Subject to any disclaimer, the term of this patent is extended or adjusted under 35 U.S.C. 154(b) by 0 days.

(21) Appl. No.: 09/762,205
(22) PCT Filed: Aug. 4, 1999
(86) PCT No.: PCT/ES99/00250
§ 371 (c)(1), (2), (4) Date: Apr. 13, 2001
(87) PCT Pub. No.: WO00/08021
PCT Pub. Date: Feb. 17, 2000

(30) Foreign Application Priority Data

Aug. 6, 1998 (ES) .............................................. 9801694

(51) Int. Cl.$^7$ ............................................. C07D 471/04
(52) U.S. Cl. ...................................................... 546/121
(58) Field of Search .......................................... 546/121

(56) References Cited

FOREIGN PATENT DOCUMENTS

FR 2600650 * 12/1987

* cited by examiner

Primary Examiner—Bernard Dentz
(74) Attorney, Agent, or Firm—Steinberg & Raskin, P.C.

(57) ABSTRACT

It comprises reducing the hydroxy ester of formula (X) by reacting it in DMF and then with an iminium salt of formula (XIII) formed in situ with thionyl chloride and dimethylformamide, and subsequent reduction with an appropriate reducing agent to form the ester of formula (XII), which is then reacted with dimethylamine in a polyhydroxylated solvent medium at an appropriate

9 Claims, No Drawings

PROCESS FOR PREPARING N,N,6-TRIMETHYL-2-(4-METHYLPHENYL)-IMIDAZO-[1,2-A]-PYRIDINE-3-ACETAMIDE AND SALTS THEREOF

FIELD OF THE INVENTION

The present invention relates to a new process for preparing N,N,6-trimethyl-2-(4-methylphenyl)-imidazo-[1,2-a]-pyridine-3-acetamide and its salts.

BACKGROUND OF THE INVENTION

N,N,6-trimethyl-2-(4-methylphenyl)-imidazo-[1,2-a]-pyridine-3-acetamide is a substance presenting clinical activity as hypnotic [P. George et al.—Actual.Chim.Thér. 18, 215 (1990), P. George et al.—Imidazopyridines in Sleep Disorders—De. J. P. Sauvanet, S. Z. Langer and P. L. Moselli—Raven Press New York, 1988, p.11], characterized by not belonging to the group of benzodiazepines, which up to now has been the basis of most drugs in use with said activity.

This substance has structural formula (I)

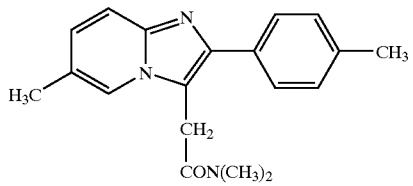

(I)

There are processes for obtaining N,N,6-trimethyl-2-(4-methylphenyl)-imidazo-[1,2-a]-pyridine-3-acetamide of formula (I) [European Patents 50563 and 251589 and French Patent 2600650] where this substance is prepared by reacting imidazo-[1,2-a]-pyridine (II) and an acetal of N,N-dimethyi-glyoxamides (formula III)

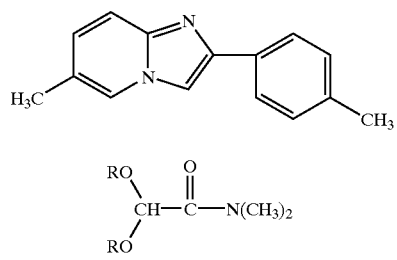

(II)

(III)

where R represents an alkyl group that yields hydroxyamide of formula (IV), without going through the ester as an intermediate product.

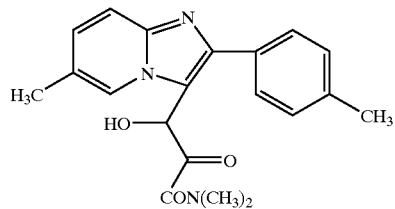

(IV)

DESCRIPTION OF THE INVENTION

The process representing the object of the present application for obtaining the substance with the structure (I), consists of reacting 2-amino-5-methyl pyridine of formula (V) with 4-methyl-haloacetophenone of formula (VI), in order to yield 6-methyl-2-(4-methylphenyl)-imidazo-[1,2-a]-pyridine of formula (II).

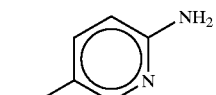

(V)

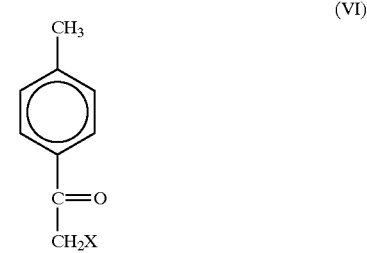

(VI)

(VII)

The first step of the reaction for obtaining (VI) from an acid halide of formula (VII), where X is Cl or Br, is carried out in toluene by adding a Lewis acid as catalyst, such as aluminum chloride or ferric chloride.

The temperature must be below 10° C.

The second step is performed in an alkali medium by adding a base such as sodium bicarbonate or potassium bicarbonate to the above solvent, to which an alcohol of one to three carbons is added.

The work temperature is between 40 and 70° C.

The 6-methyl-2-(4-methylphenyl)imidazo-[1,2-a]-pyridine (II) is reacted with methyl glyoxalate of formula (VIII) or its methyl hemiacetal (IX) to yield the hydroxy ester of formula (X), described for the first time in the invention.

(VIII)

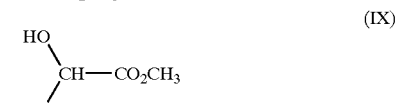

(IX)

(X)

This reaction is carried out using as solvent a halogenated hydrocarbon such as dichloromethane, chloroform, 1,2-dichloroethane or trichloroethylene at a temperature of 40 to 70° C.

Removal of the hydroxyi group is performed by substitution with a chlorine through the reaction with the iminium salt generated with thionyl chloride and dimethylformamide. The halogenated compound (XI) being formed is not isolated and it is reduced to yield the ester (XII).

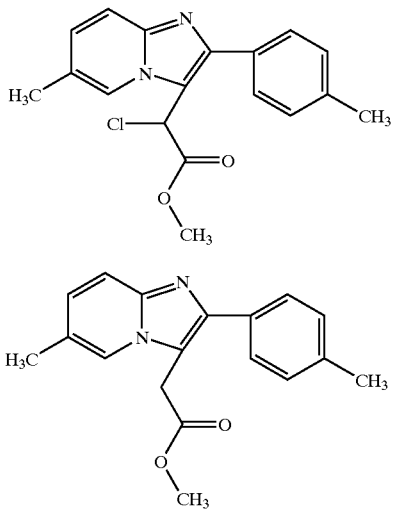

Note that the intermediate compounds (X), (XI), and (XII) obtained in the process of the invention for obtaining the compound (I) are new and have not been previously described in the literature.

In order to obtain (XI) a halocarbonated solvent such as dichloromethane, chloroform, or 1,2-dichloroethane is used at a reaction temperature of 0 to 30° C.

The reaction of (XI) to yield (XII) is carried out in the above solvent by adding a reducing substance, such as sodium hydrosulfite or sodium sulfoxylate formaldehyde.

The reaction temperature must be between 10 and 50° C.

The reaction of (XII) with dimethylamine in a polyhydroxylated solvent such as ethylene glycol or propylene glycol yields the amide (I).

The amide of formula (I), through dissolution in an alcohol such as methanol, ethanol, or isopropanol and addition of a solution of an acid such as tartaric acid, oxalic acid, or acetic acid in the same solvent, yields the corresponding salts. The molar ratio of added acid to the amide is from 0.4:1 to 1:1.

In the preparations described in the present invention, the use of the methyl ester of the glyoxylic acid (VIII) or its methyl hemiacetal (IX) has advantages over the substance (III), which is used in said patents, since these substances are more readily available and economical.

The present process also avoids the use of dangerous solvents, such as the isopropyl ether, as well as the isolation of the chlorinated compound (XI), which simplifies the process and removes a reaction step.

Another important difference of the present invention is the use of the chloro iminium salt (XIII) as a reagent for obtaining the chloro ester (XI).

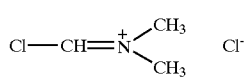

This reagent can be used in milder, and therefore more selective, conditions, which is reflected in the throughput and particularly in the purity of the obtained products. The amide (I) is obtained as colourless crystals, with a 73% yield for the transformation of the hydroxy ester (X) into the ester (XII).

The sodium sulfoxylate used for reducing the chlorinated intermediate (XI) is a simpler and more economical reagent to use than the sodium borohydride.

The following non-limitative examples include detailed processes representing the operating possibilities of the present invention.

EXAMPLE 1

6-METHYL-2-(4-METHYLPHENYL)-IMIDAZO-[1,2-a]-PYRIDINE (II)

In a 50 l reactor, put the toluene (9.4 l) and add the aluminum trichloride (3.10 kg) with stirring.

When the inner temperature of the suspension reaches a value of 0–5° C., start adding a solution of α-bromoacetyl bromide (2 l) in toluene (2.8 l). The inner temperature must not exceed 10° C. Once the addition is finished, keep the inner temperature between 2 and 10° C. for 45 minutes.

Slowly add water (13.2 l) so that the inner temperature does not exceed 50° C. and keep stirring for 1 hour. Draw off the phases and separate them.

Remove the aqueous phase again with toluene (3.6 l), join the organic phases, wash them with water (5 l), 5% sodium bicarbonate (4 l), water (4 l), and finally with a saturated sodium chloride solution (4 l).

Perform a control by thin-layer chromatography on silica gel plates with fluorescent indicator, using benzene:ethyl acetate (9:1) as developing solvent.

Place the final organic phase containing the intermediate (VI, X=Br) in a 50 l reactor and heat up to an inner temperature of about 30° C. Add then the sodium bicarbonate (2.08 kg) and a solution of 2-amino-5-methyl-pyridine (2.63 kg) in methanol (4.5 l).

Once the addition is finished heat the suspension up to an inner temperature of 58–62° C. and keep this temperature for 3 hours. Perform a control by thin-layer chromatography with the method described above.

Once the reaction is finished, cool the suspension and vacuum filter. Wash the solid with methanol (2×2.5 l and 1×1.5 l), then with hot water (1×16.6 l) and finally with water at room temperature (1×3 l).

Dry in oven at 60° C. with air flow for 10 hours until constant weight is reached. 3.8 kg (70.2%) of a slightly yellowish crystalline solid with MP: 208–208.5° C. and a title of 99.3% is obtained.

$^1$H-NMR (CDCl$_3$): δ (ppm): 7.83 (3H, d); 7.71 (1H, s); 7.51 (1H, d); 7.23 (2H, d); 6.99 (1H, dd); 2.38 (3H, s); 2.30 (3H, s).

IR (KBr) (cm$^{-1}$): 3131–2860; 1645.5; 1485.4; 1423.7; 1346.5; 825.7; 806.4; 735.0.

MS (70 eV) m/e (%): 223 (16.3); 222 (100); 221 (18.9); 220 (3.4); 92 (5.9); 65 (5.1).

EXAMPLE 2

6-METHYL-2-(4-METHYLPHENYL)-IMIDAZO-[1,2-a]-PYRIDINE-3-(α-HYDROXY)-METHYL ACETATE (X)

In a 50 l reactor, charge 1,2-dichloroethane (11 l), add the intermediate (II) (3.34 kg) with stirring, and then the anhydrous sodium acetate (0.308 kg).

Add a solution of methyl glyoxalate (VIII) (1.6 kg) in 1,2-dichloroethane (5 l) with stirring.

Start heating until reaching an inner temperature of 55° C. and keep under these conditions with stirring for 3 hours. Perform a control by silica gel thin-layer chromatography using ethyl acetate:cyclohexane (6:4) as developing solvent.

Once the reaction time indicated has finished, start the cooling of the reaction mixture.

When the suspension has cooled, vacuum filter the solid and wash with 1,2-dichloroethane (1×3.5 l and 1×1.5 l); then with water (1×13.4 l and 1×3.4 l).

Dry in oven at 60° C. with air flow until constant weight is reached.

4.31 kg (92.5%) of a colourless solid with MP: 205° C. with decomposition is obtained.

$^1$H-NMR (CDCl$_3$): δ(ppm): 7.99 (1H, s); 7.53 (2H, d); 7.47 (1H, d); 7.18 (2H, d); 7.04 (1H, d); 5.80 (1H, s); 4.05–4.3 (1H, sa); 3.71 (3H, s); 2.38 (3H, s); 2.31 (3H, s).

IR (KBr) (cm$^{-1}$): 3447.3; 1749.7; 1452.6; 1387.0; 1198.0; 1151.7; 1084.2; 823.7; 796.7.

MS (70 ev) m/e (%): 311 (2.0); 310 (9.0); 252 (19.7); 251 (100); 223 (3.6); 222 (2.0); 103 (1.1); 92 (4.4); 65 (2.8).

EXAMPLE 3

6-METHYL-2-(4-METHYLPHENYL)-IMIDAZO-[1,2-a]-PYRIDINE-3-(α-HYDROXY)-METHYL ACETATE (X)

In a 600 l reactor, charge dichloromethane (260 l), add the intermediate (II) (95 kg) with stirring, and then the anhydrous sodium acetate (8.8 kg).

Add a solution of the methyl hemiacetal of the methyl glyoxalate (IX) (75 kg) (62 l) with stirring at room temperature.

Start heating until reaching an inner temperature of 40–42° C. and keep under these conditions with stirring for 4 hours. Perform a control by silica gel thin-layer chromatography using ethyl acetate:cyclohexane (6:4) as developing solvent.

Once the reaction time indicated has finished, start the cooling of the reaction mixture up to a temperature of 5° C.

Once the suspension has cooled, centrifuge the solid and wash it with dichloromethane.

Dry in oven with air flow at room temperature.

Suspend the solid in water (355 l) at 28° C.

Centrifuge again while washing with water.

Dry with air flow at 60° C. 5 121.4 kg (91,5%) of a product with the same characteristics as the product of example 2 is obtained.

EXAMPLE 4

6-METHYL-2-(4-METHYLPHENYL)-IMIDAZO-[1,2-a]-PYRIDINE-3-METHYL ACETATE (XII)

In a 50 l reactor, put chloroform (9.6 l) and thionyl chloride (2.02 l). Cool at 5° C. and add a solution of dimethylformamide (2.0 l) in chloroform (4.0 l) with stirring. The reaction is exothermic and the room temperature is attained.

Keep stirring, at said temperature, for 45 minutes from the time the addition was started.

Cool the reaction mixture up to an inner temperature of 5–10° C. and add, in chunks and with stirring, the intermediate (X) (6.0 kg) together with another 3.3l of chloroform.

Keep stirring at room temperature for 2 hours.

Then add in chunks sodium sulfoxylate aldehyde (Rongalite) and continue stirring for 2 hours at a temperature of 38–40° C.

Heat up to 50° C., add methanol (20 l) and filter at this temperature, thoroughly washing the precipitate with methanol at 50° C.

Concentrate the filtrate by distillation at reduced pressure until a volume of about 13 litres is obtained, while removing the chloroform with methanol.

Then add water (6 l), heat up to 60° C., and filter.

Cool the filtrate down to 40° C. and add a 10% solution of sodium hydroxide (w/v) until pH 10–11.

Cool and filter.

Crystallize this raw and humid solid with methanol (20 l) by hot filtering in carbon (0.1 kg), adding water (19 l) and cooling.

Dry in oven with air flow while increasing the temperature up to 60° C.

4.16 kg (73.1%0) of a solid with MP: 133–135° C. is obtained.

$^1$H-NMR (CDCl$_3$): δ (ppm): 7.83 (1H,s); 7.70 (2H, d); 7.55 (1H, d) ; 7.27 (2H, d); 7.06 (1H, dd); 4.02 (2H, s) 3.76 (3H, s); 2.40 (3H, s); 2.35 (3H, s).

IR (KBr) (cm$^1$): 1726.6; 1392.8; 1331.1; 1228.8; 1176.8.

MS (70 ev) m/e (%): 296 (2.0); 295 (14.0); 294 (65.5); 237 (3.9); 236 (42.6); 235 (100), 233 (10.4); 221 (2.0); 220 (11.5); 219 (20.7); 92 (31.2); 86 (8.0); 84 (11.2); 65 (16).

EXAMPLE 5

N,N,6-TRIMETHYL-2-(4-METHYLPHENYL)-IMIDAZO-[1,2-a]-PYRIDINE-3-ACETAMIDE (I)

In a stainless steel reactor with a 50 l capacity, prepared to work under pressure, charge a 39% solution of dimethylamine in ethylene glycol (w/w) (7.6 l) and slowly add the intermediate with stirring (XII) (3.125 kg).

Close the equipment and heat up to a temperature of 55–65° C. so that the pressure does not exceed 35 psi.

After 3 hours, verify that the reaction has ended by thin-layer chromatography [silica gel plates with fluorescent indicator; developing solvent:cyclohexane:methylene chloride:diethylamine (7:2:1)].

Cool the suspension until the equipment is depressurized and pour it over water (12 l), contained in a stainless steel container provided with mechanical stirring. Add another 4l of water to finish pouring it into the container and clean the reactor.

Stir the suspension at room temperature for about 2 hours.

Cool at 10° C., filter, and wash with water (2×3 l).

Dry the obtained product in air flow at 60° C. until constant weight is reached.

Recrystallize the raw solid with acetonitrile (17 l).

Cool, filter, wash, and dry in oven at 60° C. with air flow until constant weight is reached.

2.84 kg (87%) of a colourless product with MP: 195–197° C. is obtained.

$^1$H-NMR (CDCl$_3$): δ (ppm): 7.98 (1H, s); 7.55 (2H, d) 7.52 (1H, d); 7.26 (2H, d); 7.04 (1H, dd); 4.07 (2H, s) 2.94 (3H, s); 2.88 (3H, s) ; 2.40 (3H, s) ; 2.35 (3H, s).

$^{13}$C-NMR (CDCl$_3$) (with decoupling of $^1$H in wideband): 166.161; 143.959; 143.682; 137.187; 131.717; 129.139;

128.217; 127.230; 121.990; 121.449; 116.355; 113.560; 37.288; 35.632; 29.973; 21.079; 18.249.

IR (KBr) (cm$^{-1}$): 2980–3005; 1635.9; 1138.2; 825.7; 794.8.

MS (70 ev) m/e (%): 309 (5.0); 308 (41.2); 307 (100); 236 (68.2); 235 (71.9); 233 (22.9); 222 (2.1); 221 (4.8); 220 (27.4); 219 (51.4) ; 92 (51.6); 65 (37.9).

| ELEMENTAL ANALYSIS: | | | |
|---|---|---|---|
| FOUND: | C: 74.36% | H: 6.92% | N: 13.56% |
| CALCD.: | C: 74.24% | H: 6.89% | N: 13.67% |

EXAMPLE 6

N,N,6-TRIMETHYL-2-(4-METHYLPHENYL)-IMIDAZO-[1,2-a]-PYRIDINE-3-ACETAMIDE-[R-(R*,R*) ]-2,3-DIHYDROXYBUTANEDIOATE (2:1).

In a 50 l reactor, charge methanol (25 l) and add substance (I) (2.44 kg).

Heat to dissolution and add a solution of L-(+) tartaric acid (0.6 kg) in methanol (4.5 l).

Concentrate by distillation until a volume of about 18l is obtained, cool and filter, while washing with the same solvent.

Dry the product in air flow, gradually increasing the temperature up to about 60° C.

2.82 kg (93%) of the reference compound with MP: 193–195° C. with decomposition is thus obtained.

IR (KBr) (anhydrous form) (cm$^{-1}$): 1645.5; 1404.4; 1344.6; 1275.1; 1147.8; 1138.2; 1115.0; 1076.4; 1022.4; 918.3; 825.7; 794.8; 719.6; 621.2; 600.0.

| ELEMENTAL ANALYSIS: | | | |
|---|---|---|---|
| FOUND: | C: 66.06% | H: 6.32% | N: 10.95% |
| CALCD.: | C: 65.97% | H: 6.28% | N: 10.99% |

What is claimed is:
1. Process for preparing N,N,6-trimethyl-2-(4-methylphenyl)-imidazo-[1,2-a]-pyridine-3-acetamide of formula (I):

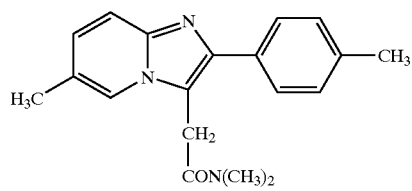

characterized in that it comprises reducing the hydroxy ester of formula (X)

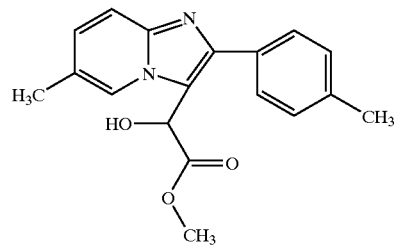

by reacting it in DMF and then with an iminium salt of formula (XIII) formed in situ with thionyl chloride and dimethylformamide,

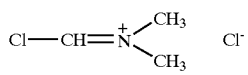

and subsequent reduction with an appropriate reducing agent to form the ester of formula (XII),

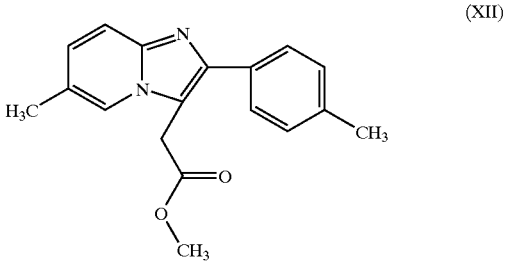

which is then reacted with dimethylamine in a polyhydroxylated solvent medium at an appropriate temperature.

2. Process according to claim 1, wherein said appropriate reducing agent used to form the ester of formula (XII) is selected from the group consisting of sodium sulfoxylate formaldehyde and sodium hydrosulfite and comprising the step of reacting said ester with dimethylamine in a polyhydroxylated solvent medium at a temperature from 30 to 70° C.

3. Process according to claim 1, wherein said 6methyl-2-(4-methylphenyl)-imidazo-(1,2-a)-pyridine-3-(α-hydroxy)-methyl acetate of formula (X) is obtained by reaction of compound (II) with methyl glyoxalate of formula (VIII) or its methyl hemiacetal of formula (IX) in a chlorinated solvent selected from the group consisting of chloroform, 1,2-dichloroethane and trichloroethylene at a temperature of 40 to 70° C.

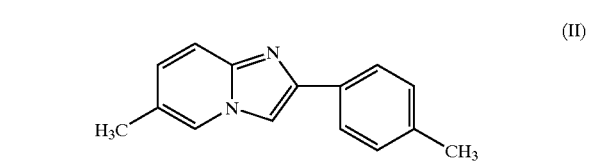

4. Process according to claim 2, characterized in that said 6-methyl-2-(4-methylphenyl)-imidazo-[1,2-a]-pyridine of formula (II) is the reaction product of 2-amino-5-methylpyridine of formula (V) with a α-halo-4-methyl acetophenone of formula (VI) (X=Cl or Br)

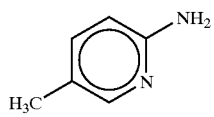
(V)

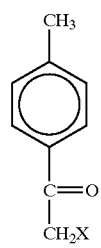
(VI)

in toluene and an alcohol of one to three carbons, by adding a base selected from a group consisting of sodium bicarbonate or potassium bicarbonate at a work temperature of 40 to 70° C.

5. Process according to claim 1, wherein the free base of formula (I) is reacted with an acid selected from the group consisting of tartaric acid, oxalic acid and acetic acid in an alcohol medium using as solvent methanol, ethanol or isopropanol with a molar ratio of acid to base between 0.4:1 and 1:1 and crystalizing the corresponding salt with a purity level appropriate for its use in human medicine.

6. The process according to claim 2, wherein said polyhydroxylated solvent medium is ethylene glycol.

7. The process according to claim 2, wherein said polyhydroxylated solvent medium is propylene glycol.

8. The process according to claim 4, wherein said base is sodium bicarbonate.

9. The process according to claim 4, wherein said base is potassium bicarbonate.

* * * * *